United States Patent
Bernardi et al.

(10) Patent No.: US 9,588,096 B2
(45) Date of Patent: Mar. 7, 2017

(54) MEASURING UNIT FOR DETERMINING THE COMPOSITION OF THE LIQUID PHASE IN A MULTI-PHASE MIXTURE

(71) Applicant: PIETRO FIORENTINI SPA, Arcugnano (VI) (IT)

(72) Inventors: Stefano Bernardi, Padua (IT); Marco Pavan, Venice (IT)

(73) Assignee: Pietro Fiorentini SPA, Arcugnano (VI) (IT)

( * ) Notice: Subject to any disclaimer, the term of this patent is extended or adjusted under 35 U.S.C. 154(b) by 258 days.

(21) Appl. No.: 14/376,385

(22) PCT Filed: Feb. 1, 2013

(86) PCT No.: PCT/IB2013/000134
§ 371 (c)(1),
(2) Date: Aug. 1, 2014

(87) PCT Pub. No.: WO2013/114194
PCT Pub. Date: Aug. 8, 2013

(65) Prior Publication Data
US 2015/0000383 A1    Jan. 1, 2015

(30) Foreign Application Priority Data
Feb. 3, 2012   (IT) ................ VI2012A0029

(51) Int. Cl.
*G01N 33/28* (2006.01)
*G01N 29/22* (2006.01)
*G01N 21/17* (2006.01)

(52) U.S. Cl.
CPC ......... *G01N 33/2835* (2013.01); *G01N 21/17* (2013.01); *G01N 29/222* (2013.01); *G01N 33/2823* (2013.01); *G01N 2201/0256* (2013.01)

(58) Field of Classification Search
CPC ........... G01N 33/2835; G01N 33/2847; G01N 21/17; G01N 29/222
(Continued)

(56) References Cited

U.S. PATENT DOCUMENTS

| 4,574,643 | A | * | 3/1986 | Scott ..................... G01F 1/74 327/104 |
| 5,203,211 | A | | 4/1993 | Jung |

(Continued)

FOREIGN PATENT DOCUMENTS

| WO | 2007/034132 A1 | 3/2007 |
| WO | 2009/149361 A1 | 12/2009 |

OTHER PUBLICATIONS

International Search Report and Written Opinion dated May 3, 2013, issued in PCT Application No. PCT/IB2013/000134, filed Feb. 1, 2013.

*Primary Examiner* — Walter L Lindsay, Jr.
*Assistant Examiner* — Ruth Labombard
(74) *Attorney, Agent, or Firm* — Workman Nydegger

(57) ABSTRACT

Measuring device (1; 15) for determining the composition of the liquid phase of a liquid-gas mixture includes a duct (2) defining a flow direction (X) of the mixture parallel to the longitudinal development axis (Y) of the duct (2) and a measuring element (4) arranged in the duct (2) and suited to determine the composition of a liquid layer that flows in contact with the internal surface (3) of the duct (2). The internal surface (3) of the duct (2) includes an intercepting surface (5, 5') suited to convey part of the liquid layer towards the measuring element (4), arranged so that it is incident on the flow direction (X) and developed according to a conveyance trajectory that has a helical section and whose tangent to the outlet end (7, 7') intersects the measuring element (4).

18 Claims, 4 Drawing Sheets

(58) Field of Classification Search
 USPC .......................................................... 73/61.44
 See application file for complete search history.

(56) References Cited

U.S. PATENT DOCUMENTS

| | | | |
|---|---|---|---|
| 6,507,401 B1 * | 1/2003 | Turner | E21B 47/102 356/417 |
| 2004/0244501 A1 | 12/2004 | Nyfors et al. | |
| 2007/0124091 A1 | 5/2007 | Wee | |

\* cited by examiner

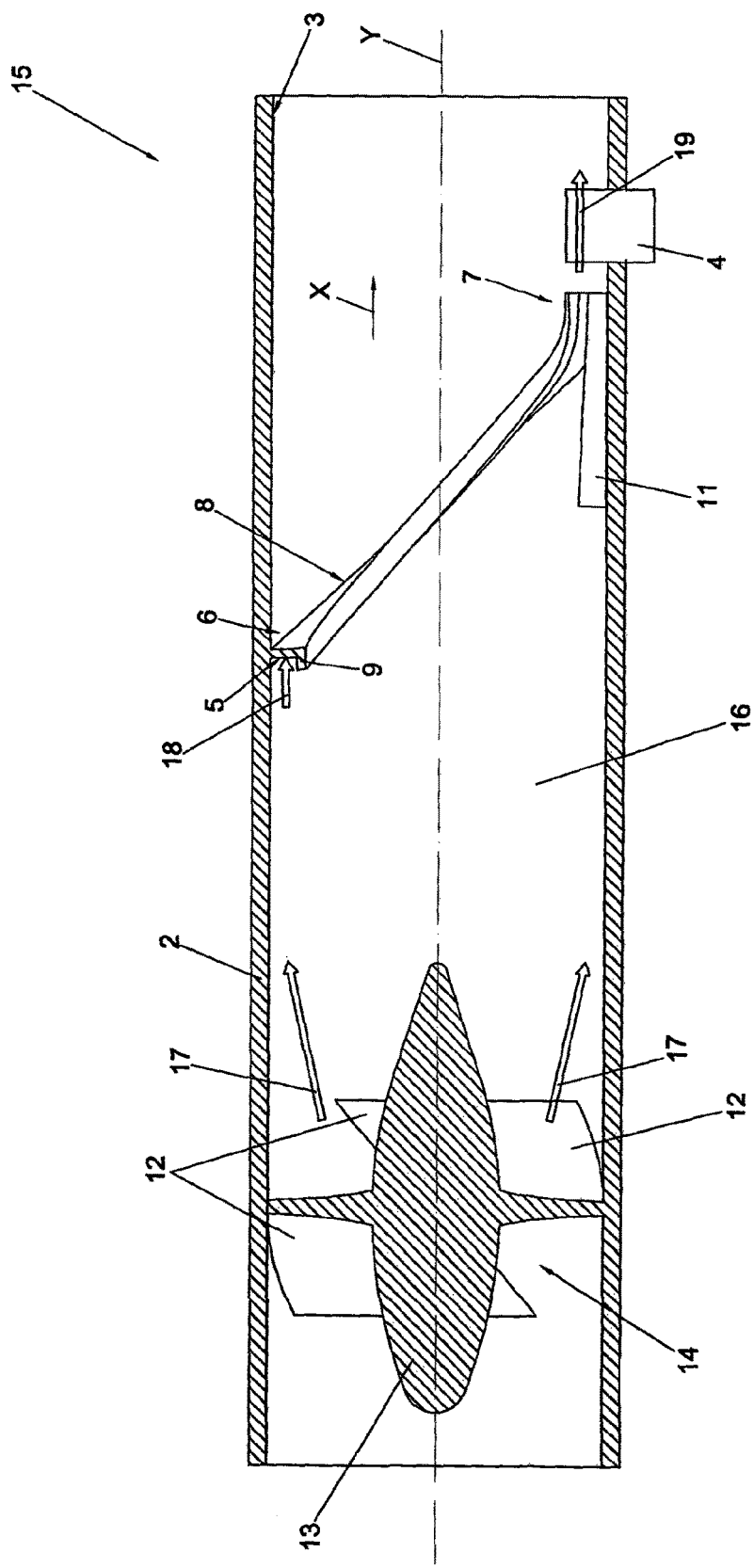

MEASURING UNIT FOR DETERMINING THE COMPOSITION OF THE LIQUID PHASE IN A MULTI-PHASE MIXTURE

BACKGROUND OF THE INVENTION

1. Field of the Invention

The present invention concerns a device for measuring the composition of a liquid contained in a multi-phase mixture, particularly suited to be used in the sector of oil extraction.

2. Present State of the Art

As is known, in the oil field there is the need to determine the composition of the multi-phase mixtures extracted from the wells, which are commonly constituted by a liquid phase, comprising oil, water and other components, if any, and by a gas phase.

One of the operations that are commonly performed to determine the characteristics of the mixture consists in measuring the composition of the liquid phase and, in particular, the water volume concentration with respect to the entire quantity of liquid commonly known as "water-cut" and the concentration of other types of liquid, with the aid of suitable probes including, for example, the well-known NIR (Near Infrared) probes, which exploit the principle of the attenuation of an infrared light beam that passes through the liquid.

These probes are inserted in the duct into which the mixture flows, so that they are hit by the flow of the mixture itself.

In the known systems, the reliability and precision of the concentration measure that can be obtained decrease with the increase of the volume percentage of the gas phase, commonly known as "gas-volume fraction" (GVF), meaning that the measure becomes less reliable and precise as the volume percentage of liquid contained in the mixture decreases.

In fact, as the GVF increases, the liquid tends to be progressively dispersed in drops that are more or less insulated within the gas flow.

Consequently, the probe is hit by said drops in a discontinuous way and this makes it difficult to carry out a reliable and precise measurement of the composition.

SUMMARY OF THE INVENTION

Therefore, the invention has the object to provide a device for measuring the composition of the liquid phase contained in a liquid-gas mixture that makes it possible to obtain results that are more reliable and precise compared to those obtained with the devices of known type, especially for low volume percentages of liquid in the mixture.

The object described above is achieved by a measuring device according to the main claim.

Further embodiments of the invention are described in the corresponding dependent claims.

Advantageously, the higher reliability of the measurement made possible by the measuring device of the invention allows the oil extracted from the well to be quantified more precisely.

BRIEF DESCRIPTION OF THE DRAWINGS

The said object and advantage, together with others which will be highlighted below, become clear in the following description of some preferred embodiments of the invention which are illustrated by way of non-limiting examples with reference to the attached drawings, wherein:

FIG. 5 shows a side sectional view of the measuring device of FIG. 4.

DETAILED DESCRIPTION OF THE PREFERRED EMBODIMENTS

Figure 1:
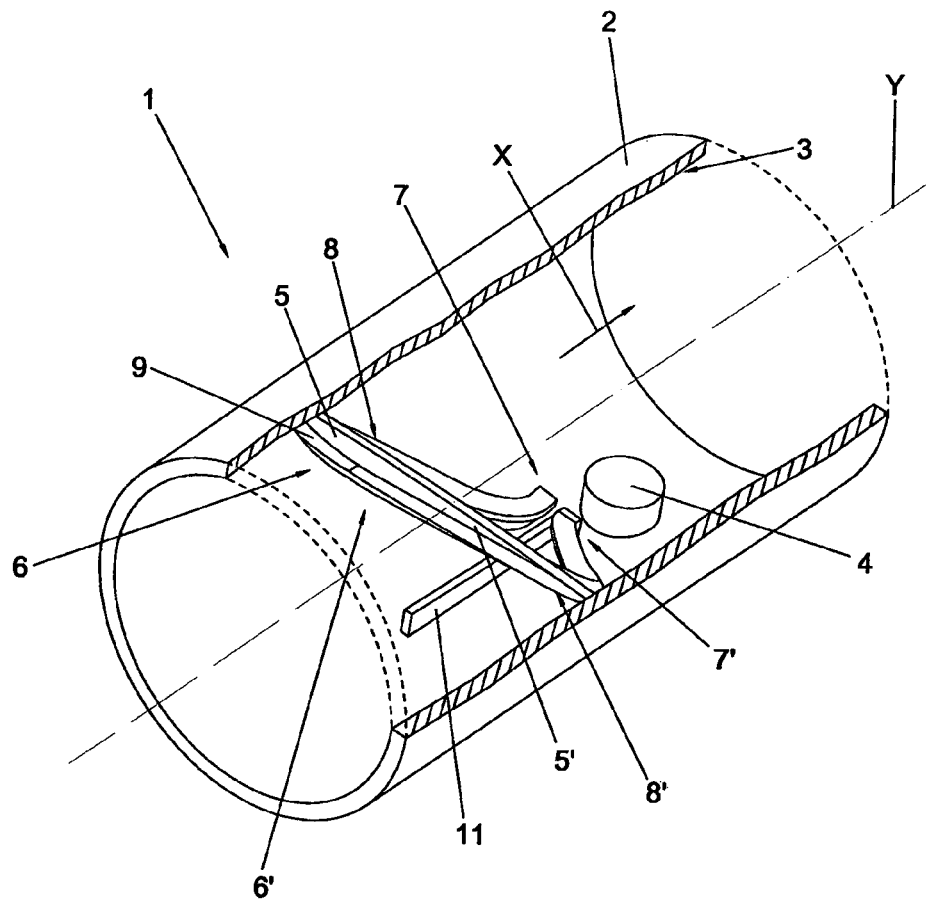
FIG. 1 shows an axonometric and partially sectional view of the measuring device of the invention, such that it is possible to see the inside of the latter.
Figure 2:
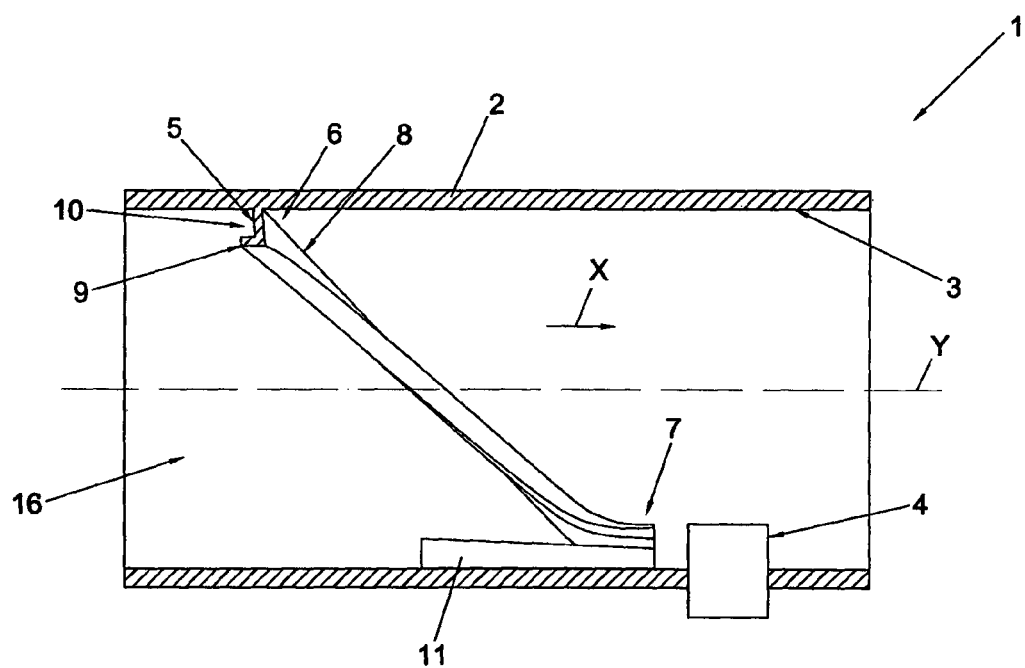
FIG. 2 shows a side sectional view of the measuring device of FIG. 1.

The measuring device that is the subject of the invention, indicated as a whole by 1 in FIG. 1, is particularly suited to be used for measuring the composition of the liquid phase in a multi-phase liquid-gas mixture extracted from an oil well.

It is obvious, however, that the invention can be applied in an analogous manner to measure the composition of a liquid contained in any liquid-gas mixture.

The measuring device 1 of the invention comprises a duct 2 that defines a longitudinal development axis Y and, in FIG. 1, is shown partially sectioned, so that it is possible to see its inside.

The mixture flows in the duct 2 according to a predefined flow direction X that is parallel to said longitudinal development axis Y.

It should be noted since now that the term "flow direction" indicates, in addition to the flow direction as correctly intended, also the sense of said flow.

The measuring device 1 also comprises a measuring element 4 suited to measure the composition of the liquid, for example its volume composition.

The measuring element 4 is arranged inside said duct 2 in proximity to the internal surface 3 of the duct 2, positioned so that it is hit by the liquid layer that flows in contact with the internal surface 3.

Advantageously, said position is particularly suitable for measuring with a high degree of reliability and precision the composition of the liquid phase when the latter is present in the mixture in a reduced volume percentage, meaning with high GVF values.

The improvement in the reliability and precision of the measurement becomes to significant with GVF values indicatively above 70% and particularly important with GVF values above 90%.

It is known, in fact, that in said conditions the liquid tends to gather and flow in a thin liquid layer (film) in contact with the internal surface 3 of the duct 2, which is entrained in the mixture flow sense, while the gas phase mainly flows in the centre area of the duct 2.

Therefore, said position of the measuring element 4 makes it possible to intercept said liquid layer in proximity to the internal surface 3.

If the measuring device 1 is used in the oil sector, the measuring element 4 can be, for example, a NIR (Near Infrared) probe of the type mentioned above, which is particularly suited to measure the volume composition of the liquid phase of the mixture.

It is evident, however, that in construction variants of the invention the measuring element 4 can be of any type, provided that it is suited to measure the composition of the liquid that hits it.

Regarding the internal surface 3 that delimits the duct 2, it comprises an intercepting surface 5 arranged so that it is incident on the flow direction X of the mixture.

Said intercepting surface 5 develops according to a predefined conveyance trajectory between an inlet end 6, arranged upstream of the measuring element 4 according to the flow direction X of the mixture, and an outlet end 7, arranged downstream of said inlet end 6 and facing the measuring element 4.

Said intercepting surface 5 makes it possible to at least partially deviate the liquid layer that flows in contact with the internal surface 3 of the duct 2, in such a way as to convey it towards the measuring element 4 along the above mentioned conveyance trajectory.

Therefore, advantageously, the intercepting surface 5 is capable of constantly directing towards the measuring element 4 a quantity of liquid that is larger than the quantity that would spontaneously reach the measuring element 4 if said intercepting surface 5 were not provided.

Consequently, the intercepting surface 5 ensures that the measuring element 4 is constantly hit by a minimum flow rate of liquid over time, in any flow condition, in particular when the gas-liquid mixture has high GVF values, meaning that it contains a reduced liquid volume percentage.

Said liquid flow rate towards the measuring element 4 makes it possible to avoid the measurement discontinuities that are typical of the known measuring devices, especially in the presence of high GVF values, thus achieving the purpose of increasing measurement reliability and precision.

Still advantageously, the conveyance of liquid produced by the intercepting surface 5 causes the mixing of the different components of the liquid itself, making the liquid that reaches the measuring element 4 more homogeneous, to further benefit of measurement stability.

Furthermore, advantageously, the conveyance action produced by the intercepting surface 5 makes it possible to use a single measuring element 4, with no need to use a plurality of measuring elements in several points of the cross section of the duct 2.

Preferably, the conveyance trajectory is configured in such a way as to define in each point a direction that comprises a component that is parallel to the longitudinal axis Y of the duct 2.

Said component advantageously makes it possible to exploit the mixture flow to entrain the liquid along the conveyance trajectory towards the measuring element 4, independently of the orientation of the duct 2.

Obviously, in the embodiments in which the duct 2 is arranged so that the mixture flows downwards, the weight of the liquid is added to said entrainment effect.

Furthermore, preferably, the conveyance trajectory is configured so that the straight line that is tangential to it at the level of said outlet end 7 intersects the measuring element 4.

In this way, advantageously, the intercepted liquid flow is directed precisely towards the measuring element 4.

Still more preferably, the conveyance trajectory comprises a section that is configured as a preferably cylindrical helix, developed around the longitudinal axis Y of the duct 2.

Advantageously, said helical configuration ensures a regular flow of the liquid along the intercepting surface 5.

Still advantageously, the helical intercepting surface 5 makes it possible to gather the liquid on a predefined angular extension of the internal surface 3 of the duct 2 without projecting excessively towards the inside of the duct itself, so as to limit any interferences in the mixture flow.

Consequently, to advantage, load losses along the duct are avoided.

Still advantageously, the reduced overhang of the intercepting surface 5 facilitates the passage of foreign bodies that are often present in oil mixtures, like for example stones, preventing them from getting stuck and obstructing the duct 2.

Preferably, the intercepting surface 5 belongs to a projecting profile 8 facing is towards the inside of the duct 2, which ensures an especially effective interception of the liquid layer, as it defines a wall that intersects the flow of the liquid.

Figure 3:
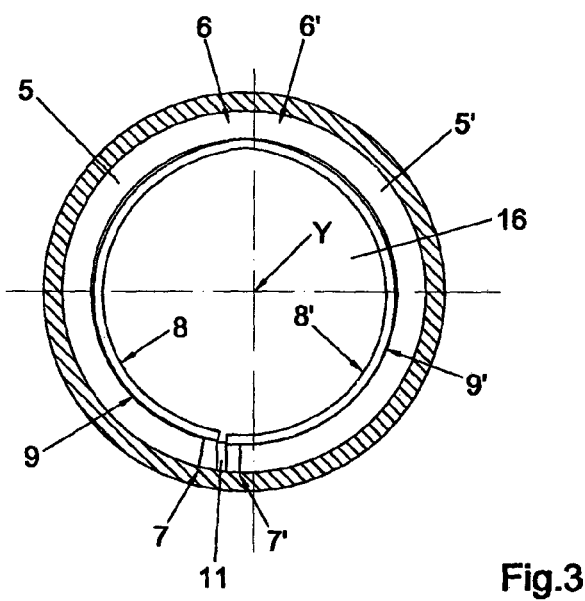
FIG. 3 shows a front sectional view of the measuring device of FIG. 1.

Preferably, and as shown in FIG. 3, the height of the profile 8 projecting towards the inside of the duct 2 is such as to leave a central zone 16 of the duct 2 free, said zone being coaxial with the longitudinal axis Y, in such a way as to minimize the obstruction of the mixture flow.

More precisely, the projecting profile 8 is preferably such as to define an intercepting surface 5 whose height is sufficient to intercept the layer of liquid flowing in contact with the internal wall 3 of the duct 2 with high GVF values, in particular exceeding 70%.

Furthermore, the projecting profile 8 is preferably delimited by a containment edge 9 that protrudes, with respect to the intercepting surface 5, in the direction opposite the flow direction X of the mixture.

It can be understood that the containment edge 9, together with the intercepting surface 5 and with the portion of the internal surface 3 adjacent to it and facing the containment edge 9, delimits a flow channel 10 that, advantageously, makes it possible to convey the liquid in a particularly effective manner.

Advantageously, the containment edge 9 guides the liquid gathered by the intercepting surface 5 and conveys it more effectively towards the measuring element 4.

Advantageously, when the intercepting surface 5 extends over an area of the internal surface 3 that faces downwards, the containment edge 9 prevents the liquid from falling from said area.

It can thus be understood that the containment edge 9 makes it possible to intercept and convey the liquid that flows on an area of the internal surface 3 with large angular extension around the longitudinal axis Y, exceeding 90° and, to the utmost, even 180°, with any orientation of installation.

According to a construction variant of the invention not illustrated herein, the intercepting surface belongs to a groove obtained in the internal surface 3 of the duct 2.

In this case, the liquid that flows in contact with the internal surface 3 passes into said groove and is then conveyed towards the measuring element 4.

Preferably, the measuring device 1 comprises a second intercepting surface is 5', developed around the longitudinal axis Y of the duct 2 according to an angular direction opposite the direction corresponding to the intercepting surface 5 already described above.

This, advantageously, makes it possible to intercept the liquid on both sides of the measuring element 4, increasing the quantity of liquid collected and the effectiveness of the conveyance operation.

Preferably, the outlet ends 7, 7' of the intercepting surfaces 5, 5' are arranged symmetrically with respect to a plane passing through the measuring element 4 and parallel to the longitudinal axis Y of the duct 2.

Advantageously, said symmetry makes it possible to convey the two liquid flows coming from the two intercepting surfaces 5, 5' into a single flow that streams in contact with the measuring element 4.

Preferably, and as shown in FIG. 3, the two intercepting surfaces 5, 5' are connected at the level of the corresponding inlet ends 6, 6', so as to be able to intercept the liquid that flows in contact with the entire internal surface 3 of the duct 2.

Preferably, the measuring device 1 comprises also a projecting partition wall 11, interposed between said outlet ends 7, 7', preferably in a central position with respect to them and preferably oriented longitudinally according to the axis Y.

Said partition wall 11 advantageously makes it possible to avoid the impact of the two flows, preventing possible deviations of the outgoing flow and its partial dispersion.

Therefore, the partition wall 11 makes it possible to obtain an outward direction of the outgoing flow that is more stable and more consistent with that required by the measuring element 4.

Figure 4:
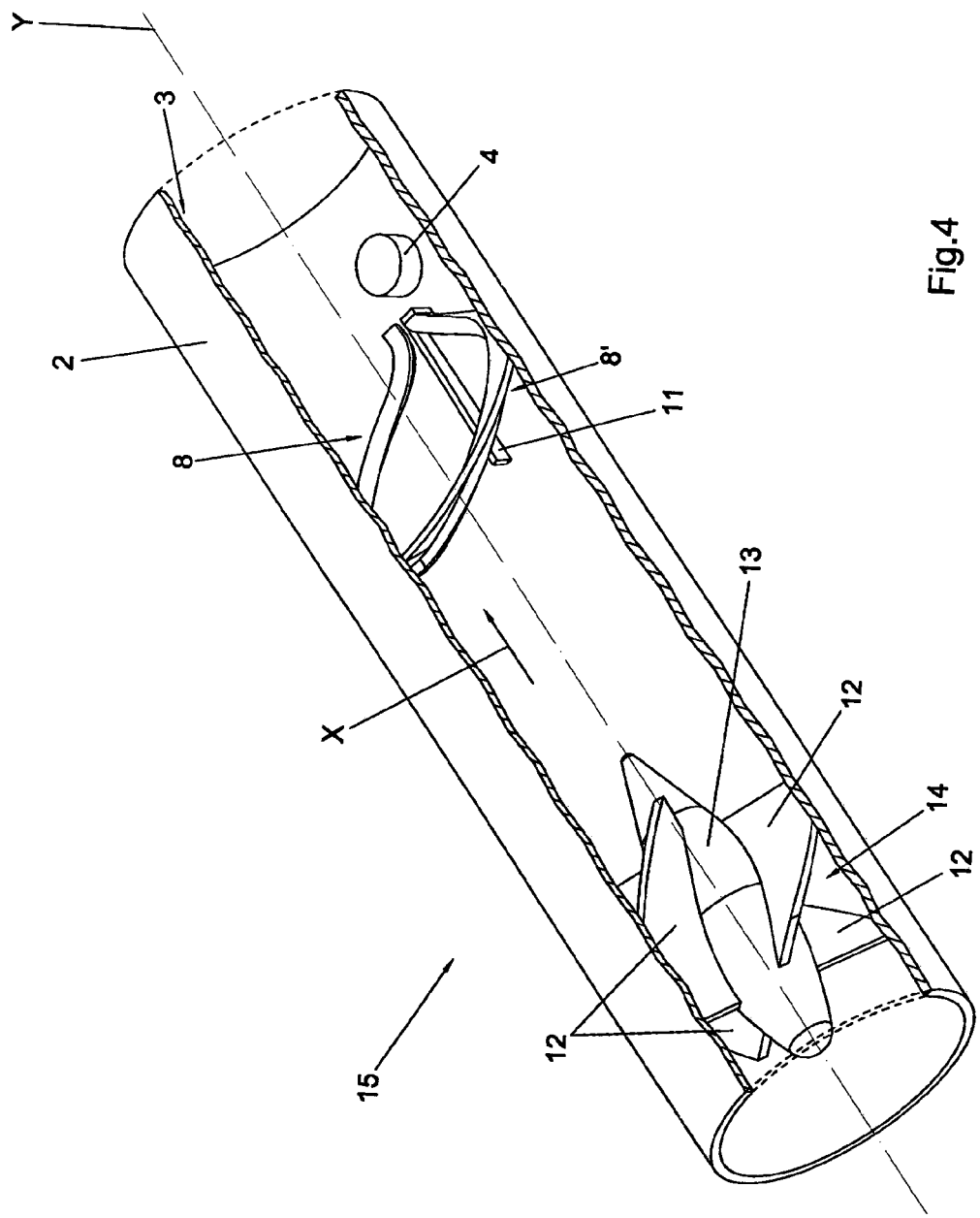
FIG. 4 shows an axonometric and partially sectional view of a construction variant of the measuring device of the invention, such that it is possible to see the inside of the same.

A construction variant of the invention, shown in FIG. 4, concerns a measuring device 15 that differs from the one described up to now in that it comprises also a plurality of guide walls 12 incident on the flow direction X, arranged upstream of the intercepting surfaces 5, 5' according to the flow direction X.

Said guide walls 12 induce in the motion of the mixture a rotary component that, due to the centrifugal effect, pushes the liquid that is located in the central area of the duct 2 towards its internal surface 3, with the advantage that said liquid is intercepted by the intercepting surfaces 5, 5' arranged further is downstream.

Said advantage is particularly useful, for example, downstream of a curve of the duct 2, where there are turbulence phenomena and deviations that cause the detachment of part of the liquid adhering to the internal surface 3, with a consequent repeated mixing of the same in the mixture.

Preferably, and as shown in FIG. 5, each guide wall 12 is delimited on a first edge by the internal surface 3 and, on a second edge, by a central body 13 that is coaxial with the duct 2, in such a way as to define corresponding guide channels 14 separated from each other.

Preferably, the shape of the guide walls 12 is such as to define for said guide channels 14 a helical development pattern.

Obviously, in construction variants of the invention, the number of said guide walls 12 can be different from that represented in the figures and said number may even be one only.

The arrows 17, 18 and 19 in FIG. 5 schematically show the flow of the liquid along the measuring device 15 of the invention.

In particular, the arrows 17 indicate the flow of the liquid towards the internal surface 3 of the duct, caused by the rotation induced in the mixture by the guide walls 12.

The liquid flow 18 in contact with the internal surface 3 is intercepted by the intercepting surfaces 5, 5' and conveyed as a single flow 19 towards the measuring element 4.

The explanation provided above shows that the measuring device for measuring the composition of liquids according to the invention offers higher measurement reliability and precision than the measuring devices of the known type, especially in the presence of high GVF values, meaning with reduced volume percentages of the liquid phase in the mixture.

In fact, the intercepting surfaces make it possible to intercept the liquid that flows on a wide area of the internal surface of the duct and to convey it towards the measuring element.

Further construction variants of the invention, even if they are neither described herein nor illustrated in the drawings, must all be considered protected by the present patent, provided that they fall within the scope of the following claims.

Where technical features mentioned in any claim are followed by reference signs, those reference signs have been included for the sole purpose of increasing the intelligibility of the claims and accordingly such reference signs do not have any limiting effect on the protection of each element identified by way of example by such reference signs.

The invention claimed is:

1. A measuring device for determining the composition of the liquid phase of a liquid-gas mixture, comprising:
   a duct into which said mixture can flow according to a predefined flow direction parallel to a longitudinal development axis of said duct, said duct having an internal surface;
   a measuring element arranged inside said duct, positioned in such a way as to be able to determine the composition of a layer of liquid that flows in contact with the internal surface of said duct;
   said internal surface of said duct comprising a helical intercepting surface arranged so that it is incident on said flow direction and developed according to a predefined helical conveyance trajectory between an inlet end, arranged upstream of said measuring element according to said flow direction, and an outlet end, arranged downstream of said inlet end and facing said measuring element, said helical intercepting surface being suited to deviate a part of said liquid layer in such a way as to convey it along said predefined helical conveyance trajectory and towards said measuring element while leaving a flow of a remaining portion of said mixture unaffected.

2. The measuring device according to claim 1, wherein said predefined helical conveyance trajectory is configured so that the tangent to said predefined helical conveyance trajectory at the level of said outlet end intersects said measuring element.

3. The measuring device according to claim 1, wherein said predefined helical conveyance trajectory defines, a direction which is provided with a component that is parallel to said longitudinal development axis.

4. The measuring device according to claim 1, wherein said helical intercepting surface at least partially bounds a flow channel obtained in said internal surface of said duct.

5. The measuring device according to claim 1, wherein said helical intercepting surface belongs to a profile projecting towards the inside of said duct.

6. The measuring device according to claim 5, wherein said projecting profile is delimited by a containment edge that projects from said helical intercepting surface in the opposite direction with respect to said flow direction, cooperating with said helical intercepting surface in order to delimit a flow channel for said liquid phase.

7. The measuring device according to claim 5, further comprising at least two of said helical intercepting surfaces being developed around said longitudinal development axis according to mutually opposing angular directions.

8. The measuring device according to claim 7, wherein said helical intercepting surfaces have outlet ends that are arranged symmetrically with respect to a plane which is parallel to said longitudinal development axis and which passes through said measuring element.

9. The measuring device according to claim 7, further comprising a projecting partition wall interposed between said outlet ends, suited to separate the liquid flows conveyed by said helical intercepting surfaces.

10. The measuring device according to claim 1, further comprising one or more guide walls incident on said flow direction and arranged in said duct upstream of said helical intercepting surface according to said flow direction, suited to induce a rotation in the flow of said mixture.

11. The measuring device according to claim 10, wherein each one of said guide walls is delimited on a first edge by said internal surface of said duct and on a second edge by a central body coaxial with said duct, in such a way as to define corresponding guide channels.

12. The measuring device according to claim 11, wherein said guide channels develop according to a helical pattern.

13. The measuring device according to claim 1, wherein said helical intercepting surface extends around said longitudinal development axis for an angle of at least 90°.

14. A measuring device for determining the composition of the liquid phase of a liquid-gas mixture, comprising:
- a duct having a tubular interior face that bounds a passage through which said mixture can flow according to a predefined flow direction parallel to a longitudinal development axis of said duct;
- a measuring element at least partially disposed within said duct, said measuring element being positioned so as to be able to determine the composition of a layer of liquid that flows in contact with said tubular interior face of said duct;
- an elongated first intercepting surface projecting inward from said tubular interior surface and extending along a longitudinal length of said tubular interior surface in a helical path, said first intercepting surface being disposed upstream of said measuring element with a tail end of said first intercepting surface being directed toward said measuring element; and
- a first containment edge outwardly projecting from said first intercepting surface along a length thereof so as to form a first elongated flow channel between the first intercepting surface and said first containment edge, said first intercepting surface and said first containment edge being configured to deviate at least a portion of said layer of liquid that flows in contact with said tubular interior face toward said measuring element.

15. The measuring device according to claim 14, further comprising:
- an elongated second intercepting surface projecting inward from said tubular interior surface and extending along a longitudinal length of said tubular interior surface in a helical path, the helical path of said second intercepting surface curving in a direction opposite to said helical path of said first intercepting surface, said second intercepting surface being disposed upstream of said measuring element with a tail end of said first intercepting surface being directed toward said measuring element; and
- a second containment edge outwardly projecting from said second intercepting surface along a length thereof so as to form a second elongated flow channel between the second intercepting surface and said second containment edge, said second intercepting surface and said second containment edge being configured to deviate at least a portion of said layer of liquid that flows in contact with said tubular interior face toward said measuring element.

16. The measuring device according to claim 15, further comprising a partition wall projecting from said tubular interior face into said passage at a location between said first intercepting surface and said second intercepting surface.

17. The measuring device according to claim 16, wherein said first intercepting surface and said second intercepting surface each have a first end and an opposing second end, said first end of said first intercepting surface and said second intercepting surface being connected together and said second end of said first intercepting surface and said second intercepting surface being spaced apart.

18. The measuring device according to claim 14, wherein the first containment edge orthogonally projects from the first intercepting surface.

* * * * *